(12) United States Patent
Zhu et al.

(10) Patent No.: US 9,181,175 B2
(45) Date of Patent: Nov. 10, 2015

(54) PROCESS FOR MANUFACTURE AND RESOLUTION OF 2-ACYLAMINO-3-DIPHENYLPROPANOIC ACID

(71) Applicants: Guoliang Zhu, Zhejian (CN); Lijun Yang, Zhejian (CN); Ying Lin, Zhejian (CN); Jie Ying, Zhejian (CN)

(72) Inventors: Guoliang Zhu, Zhejian (CN); Lijun Yang, Zhejian (CN); Ying Lin, Zhejian (CN); Jie Ying, Zhejian (CN)

(73) Assignee: Zhejiang Jiuzhous Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/193,503

(22) Filed: Feb. 28, 2014

(65) Prior Publication Data

US 2014/0179947 A1    Jun. 26, 2014

Related U.S. Application Data

(62) Division of application No. 13/144,340, filed as application No. PCT/CN2010/070144 on Jan. 12, 2010, now Pat. No. 8,703,990.

(30) Foreign Application Priority Data

Jan. 13, 2009 (CN) .......................... 2009 1 0045210

(51) Int. Cl.
| | |
|---|---|
| *C07C 229/00* | (2006.01) |
| *C07C 231/12* | (2006.01) |
| *C07C 231/20* | (2006.01) |
| *C07C 233/47* | (2006.01) |
| *C07C 233/87* | (2006.01) |
| *C07B 53/00* | (2006.01) |

(52) U.S. Cl.
CPC ............... *C07C 231/12* (2013.01); *C07B 53/00* (2013.01); *C07C 231/20* (2013.01); *C07C 233/47* (2013.01); *C07C 233/87* (2013.01); *C07B 2200/07* (2013.01)

(58) Field of Classification Search
CPC .. C07C 231/12; C07C 231/20; C07C 233/47; C07C 233/87; C07B 2200/07; C07B 53/00
USPC ............................................. 560/41; 562/450
See application file for complete search history.

(56) References Cited

U.S. PATENT DOCUMENTS

| | | | | |
|---|---|---|---|---|
| 8,703,990 | B2 * | 4/2014 | Zhu et al. | ......................... 560/41 |
| 2007/0032658 | A1 | 2/2007 | Hamada | |

FOREIGN PATENT DOCUMENTS

| | | |
|---|---|---|
| CN | 1623980 A | 6/2005 |
| JP | 61227555 A2 | 10/1986 |
| JP | 2003261522 A2 | 9/2003 |
| WO | 9847876 A1 | 10/1998 |
| WO | 03059345 A1 | 7/2003 |
| WO | WO03/055867 A1 | 7/2003 |
| WO | WO2005/061440 A1 | 7/2005 |

OTHER PUBLICATIONS

Yabe, Yuichiro et al., Chem. & Pharm. Bulletin, 1976, vol. 24, No. 12, pp. 3149-3157, ISSN:0009-2363.
Inguimbert, N et al. Journal of Peptide Research, 2004, vol. 63, No. 2, pp. 99-107, ISSN:1397-002X.
Boeriu Carmen, Rev. roum. Biochim., 29, 2, pp. 89-95 (1992).
Dion M, Biotechnology letters, Sep. 1995, vol. 17, No. 9, pp. 905-910.
Ksander G M et. al, "Dicarboxylic Acid Dipeptide Neutral Endopeptidase Inhibitors", Journal of Medicinal Chemistry, American Chemical Society, US., Jan. 1, 1995; vol. 38, No. 10, pp. 1689-1700.

* cited by examiner

*Primary Examiner* — Brandon Fetterolf
*Assistant Examiner* — Blaine G Doletski
(74) *Attorney, Agent, or Firm* — Matthew Mulkeen; David Kurlandsky

(57) ABSTRACT

The invention relates to a novel process, novel process steps and novel intermediates useful in the synthesis of pharmaceutically active compounds, in particular neutral endopeptidase (NEP) inhibitors.

19 Claims, No Drawings

PROCESS FOR MANUFACTURE AND RESOLUTION OF 2-ACYLAMINO-3-DIPHENYLPROPANOIC ACID

FIELD OF THE INVENTION

The invention relates to a novel process, novel process steps and novel intermediates useful in the synthesis of pharmaceutically active compounds, in particular neutral endopeptidase (NEP) inhibitors.

BACKGROUND OF THE INVENTION

The present invention relates to a method to prepare N-acyl derivatives of biphenyl alanine. N-acyl derivatives of biphenyl alanine are key intermediates in the synthesis of pharmaceutically active compounds, in particular neutral endopeptidase (NEP) inhibitors, such as those described in U.S. Pat. No. 4,722,810, U.S. Pat. No. 5,223,516, U.S. Pat. No. 4,610,816, U.S. Pat. No. 4,929,641, South African Patent Application 84/0670, UK 69578, U.S. Pat. No. 5,217,996, EP 00342850, GB 02218983, WO 92/14706, EP 00343911, JP 06234754, EP 00361365, WO 90/09374, JP 07157459, WO 94/15908, U.S. Pat. No. 5,273,990, U.S. Pat. No. 5,294,632, U.S. Pat. No. 5,250,522, EP 00636621, WO 93/09101, EP 00590442, WO 93/10773, WO2008/031567 and U.S. Pat. No. 5,217,996.

Typically, synthetic methods to prepare biphenyl alanine derivatives use expensive starting materials such as non-natural D-tyrosine. Moreover, said methods require the use of trifluoromethanesulfonic anhydride, which is also expensive, to activate the phenolic hydroxyl in order to carry out the aryl coupling reaction leading to the desired biphenyl structure. One example of such a synthetic approach is described in the *Journal of Medicinal Chemistry* 1995, Vol. 38 No. 10. 1689-1700. Scheme 1 illustrates one of these methods:

Scheme 1

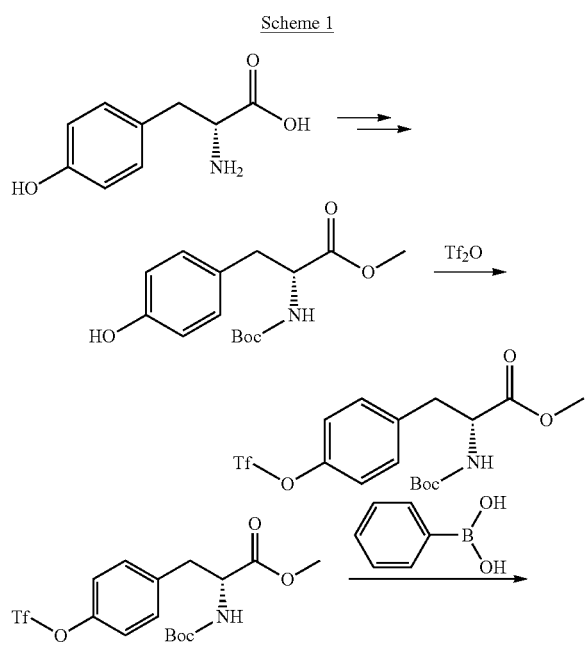

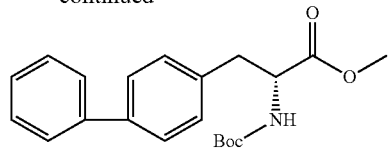

A method for preparing 2-acetylamino-3-biphenyl propanoic acid is reported in *Chemical and Pharmaceutical Bulletin,* 1976, 24 (12), 3149-57. Said method comprises the steps i) and ii) outlined below:

Step i)

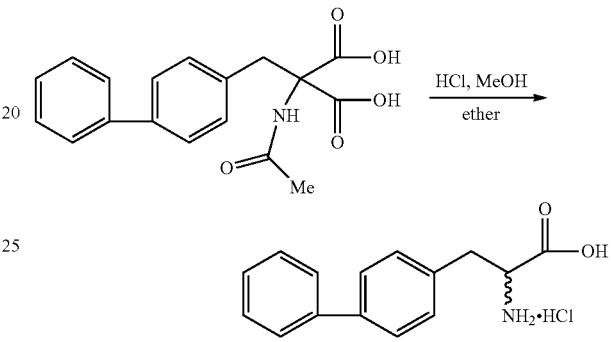

Step ii)

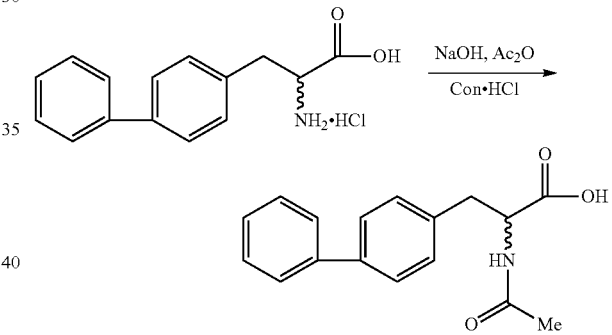

A drawback of this process is that the acetyl group is removed under the reaction conditions of the first step and thus a further chemical step is necessary in order to reinstall it. Such an undesired acetyl removal makes thus the process unattractive both from the atom economic point of view and from the reagent cost perspective. Moreover, this process does not provide means to obtain enantiomerically pure 2-acylamino-3-biphenyl propanoic acid, in particular it does not allow for the preparation of (S)-2 acylamino-3-biphenyl acid, which is, as above mentioned, a key intermediate in the synthesis of pharmaceutically active compounds, in particular neutral endopeptidase (NEP) inhibitors.

Therefore, there is a strong need to develop inexpensive methods to prepare biphenyl alanine derivatives. It is found that the present invention meets this objective and thus provides a process that is industrially advantageous.

SUMMARY OF THE INVENTION

This invention provides a method for preparing a N-acyl-biphenyl alanine of formula (I), as defined herein. The new process, according to the present invention, for producing a chiral compound according to formula (I), is summarized in Scheme 2, wherein steps a), b) and c) are as defined herein;

compounds of formula (I), (II), (III) and (IV) are as defined herein; and

"*" means a chiral center with absolute stereochemistry (R) or (S),

Scheme 2

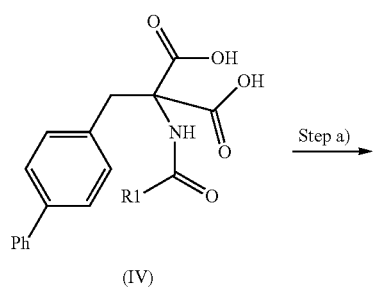
(IV)

Step a) →

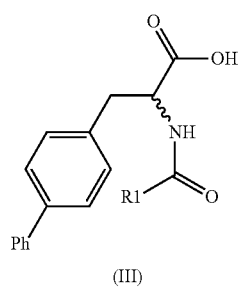
(III)

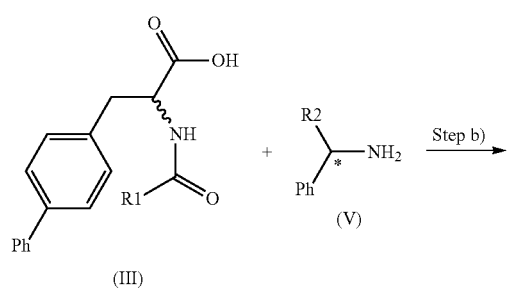
(III) + (V) Step b) →

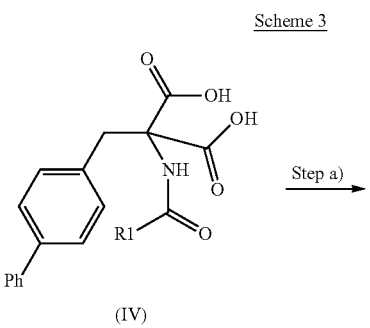
(II)

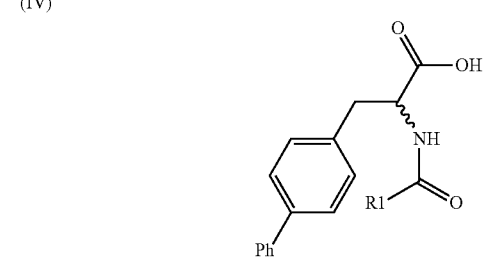
(II) Step c) →

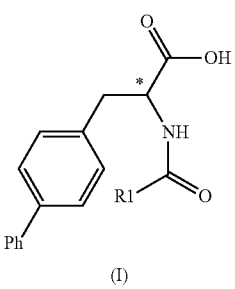
(I)

In one embodiment, the process of the present invention provides a compound of formula (Ia), as summarized in Scheme 3, wherein steps a), b) and c) are as defined herein; and compounds of formula (Ia), (IIa), (III) and (IV) are as defined herein.

Scheme 3

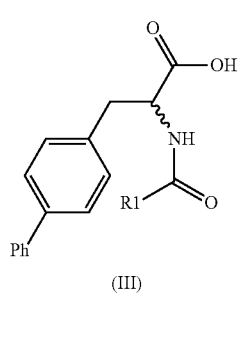
(IV)

Step a) →

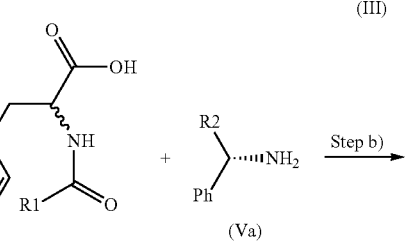
(III)

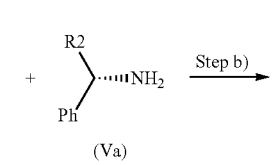
(III) + (Va) Step b) →

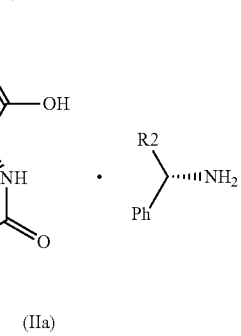
(IIa)

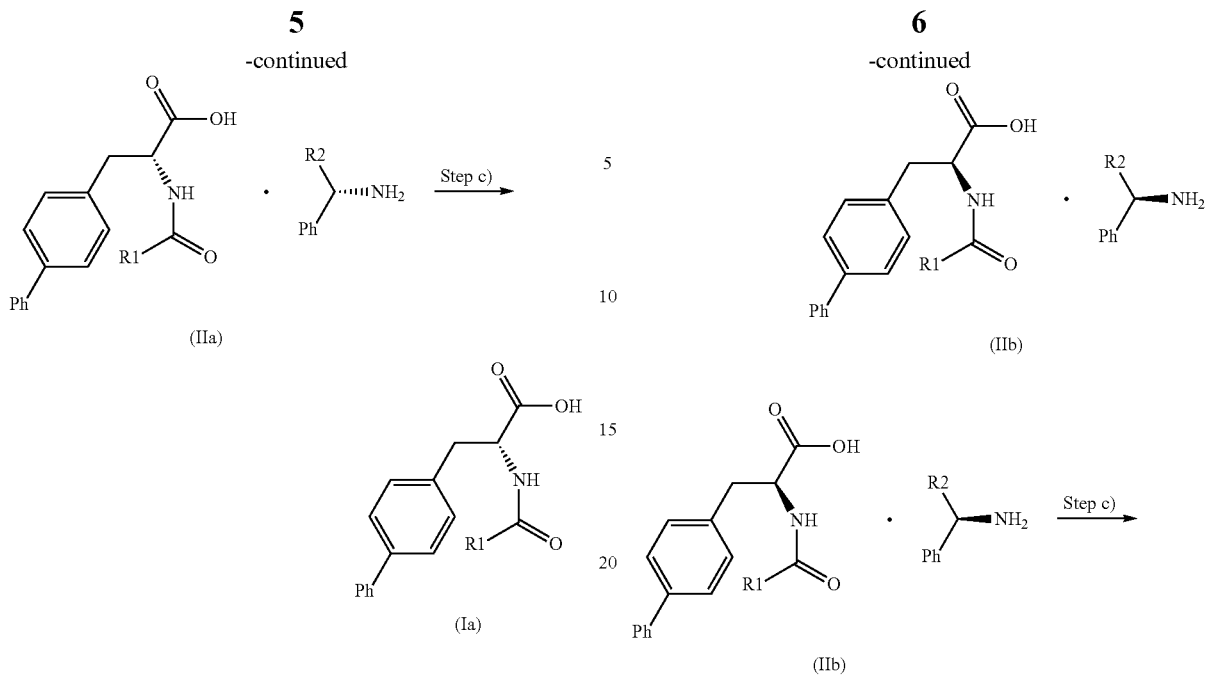

In another embodiment, the process of the present invention provides a compound of formula (Ib), as summarized in Scheme 4, wherein steps a), b) and c) are as defined herein; and compounds of formula (Ib), (IIb), (III) and (IV) are as defined herein.

Scheme 4

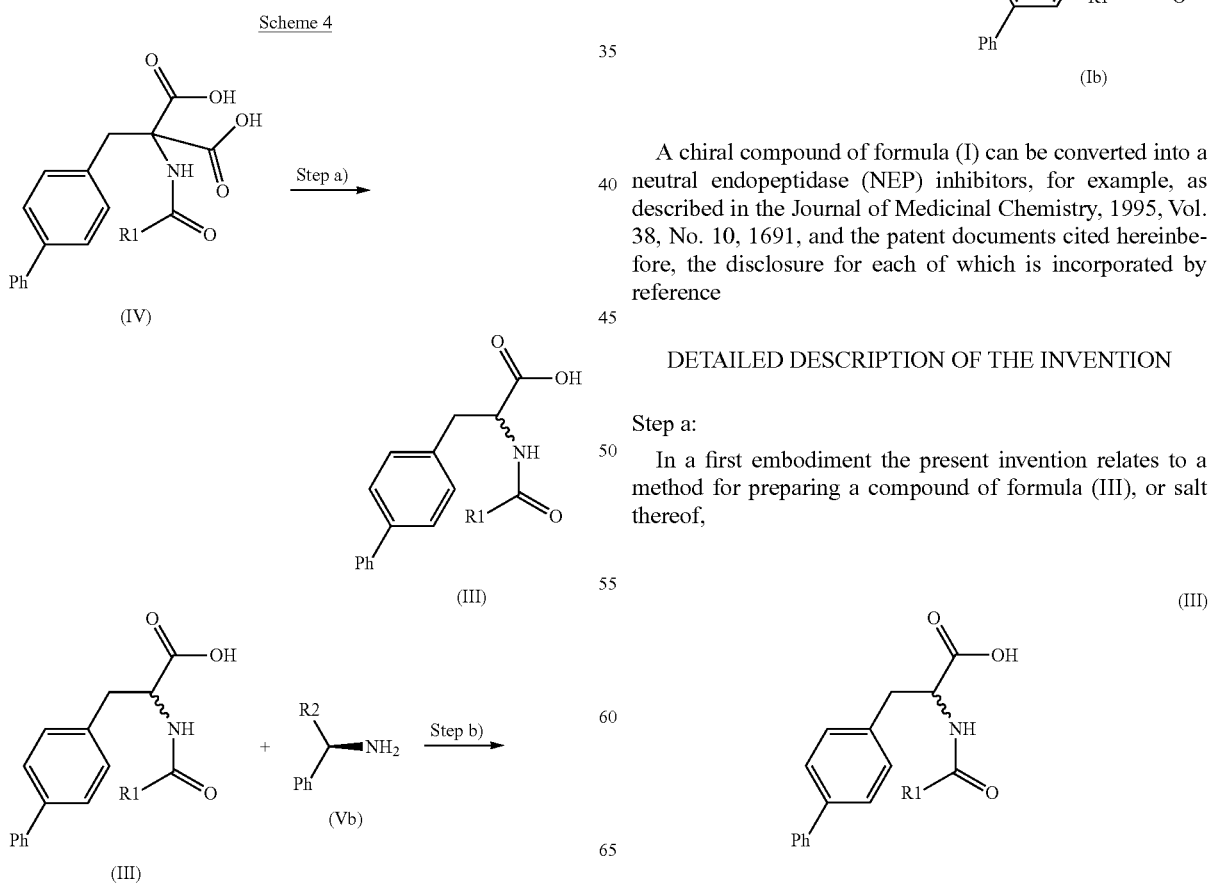

A chiral compound of formula (I) can be converted into a neutral endopeptidase (NEP) inhibitors, for example, as described in the Journal of Medicinal Chemistry, 1995, Vol. 38, No. 10, 1691, and the patent documents cited hereinbefore, the disclosure for each of which is incorporated by reference

DETAILED DESCRIPTION OF THE INVENTION

Step a:

In a first embodiment the present invention relates to a method for preparing a compound of formula (III), or salt thereof,

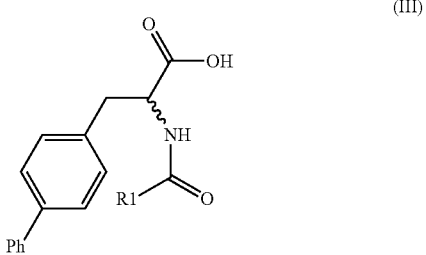

wherein

R1 is $C_{1-7}$alkyl, such as methyl or ethyl; or is substituted or unsubstituted $C_{6-10}$aryl, such as phenyl or para-chlorophenyl;

comprising reacting a compound of formula (IV), or salt thereof,

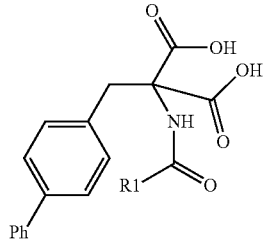

(IV)

wherein R1 is as defined for the compound of formula (III)

under decarboxylation reaction conditions to provide the compound of formula (III).

Step a) may be carried out in solvents generally known in the art, for example, in the presence of a solvent, (named solvent 1), selected from water, toluene, xylene, ethylbenzene, chlorobenzene, dichlorobenzene, nitrobenzene, N,N-dimethyl formamide (DMF) and 1-methyl-2-pyrrolidone (NMP). The amount of said solvent 1 is, for example, 0 to 50 times the feed amount (by weight) of the compound of formula IV, as defined herein.

Typically, decarboxylation reaction conditions are achieved by heating, in particular, step a is carried out at a reaction temperature of from 80 deg C. to 250 deg C. In one embodiment, step a) is carried out at the reflux temperature of solvent 1, as defined herein.

In one embodiment, the reaction time for step a) is of from 2 to 48 hours.

Step b:

In a further embodiment, the present invention relates to a method for preparing a chiral compound of formula (II),

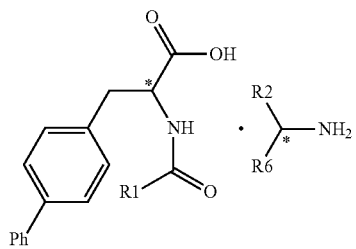

(II)

wherein

R1 is $C_{1-7}$alkyl, such as methyl or ethyl; or is substituted or unsubstituted $C_{6-10}$aryl, such as phenyl or para-chlorophenyl;

R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl;

R6 is $C_{6-10}$aryl, such as phenyl, and

"*" means a chiral center with absolute stereochemistry (R) or (S), comprising reacting a compound of formula (III), or salt thereof,

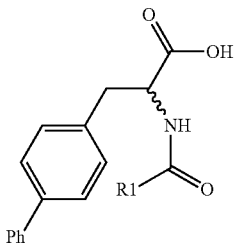

(III)

wherein R1 is as defined for the compound of formula (II), with a chiral amine of formula (V)

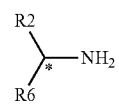

wherein R2 and R6 are as defined for the compound of formula (II), and

"*" means a chiral center with absolute stereochemistry (R) or (S);

and resolving the resulting diastereomeric mixture via crystallization to provide the compound of formula (II).

A chiral compound of formula (II), as defined herein, means a compound having the formula

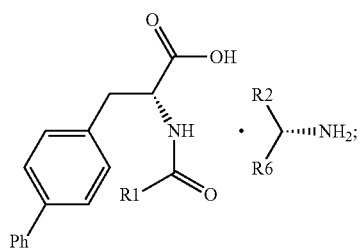

(IIa)

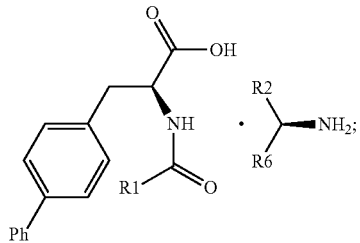

(IIb)

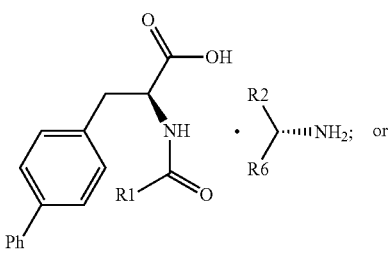

(IIc)

-continued

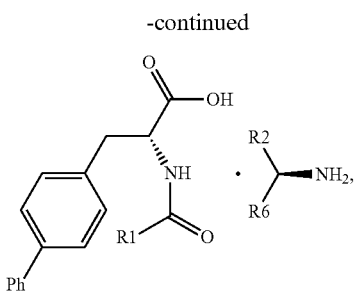

(IId)

wherein R1, R2 and R6 are as defined for the compound of formula (II).

In a further embodiment, the present invention relates to a method for preparing a chiral compound of formula (IIa),

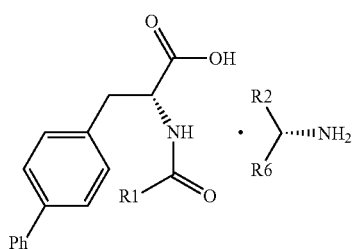

(IIa)

wherein
R1 is $C_{1-7}$alkyl, such as methyl or ethyl; or is substituted or unsubstituted $C_{6-10}$aryl, such as phenyl or para-chlorophenyl; R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl; and R6 is $C_{6-10}$aryl, such as phenyl;
comprising
reacting
a compound of formula (III), or salt thereof,

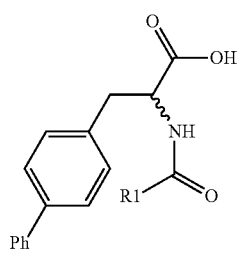

(III)

wherein R1 is as defined for the compound of formula (IIa), with a chiral amine of formula (Va)

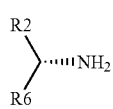

wherein R2 and R6 are as defined for the compound of formula (IIa);
and resolving the resulting diastereomeric mixture via crystallization
to provide the compound of formula (II).

In a further embodiment, the present invention relates to a method for preparing a chiral compound of formula (IIb),

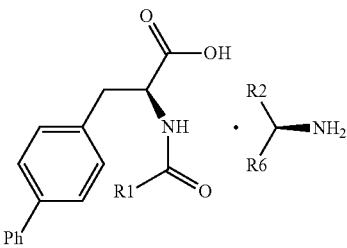

(IIb)

wherein
R1 is $C_{1-7}$alkyl, such as methyl or ethyl; or is substituted or unsubstituted $C_{6-10}$aryl, such as phenyl or para-chlorophenyl; R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl; R6 is $C_{6-10}$aryl, such as phenyl;
comprising
reacting
a compound of formula (III), or salt thereof,

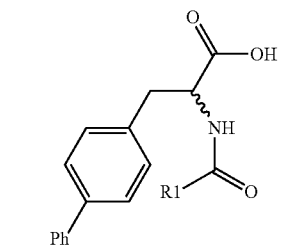

(III)

wherein R1 is as defined for the compound of formula (IIb), with a chiral amine of formula (Vb)

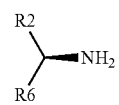

wherein R2 and R6 are as defined for the compound of formula (IIb);
and resolving the resulting diastereomeric mixture via crystallization
to provide the compound of formula (IIb).

The reactions described above are carried out in solvents generally known in the art, for example, a solvent (named solvent 2) selected from methanol, ethanol, isopropanol and aqueous solutions thereof. And the solvent added for the crystallization can be different from that added in the preparation of a compound of formula (III). The feed amount (by weight) of solvent 2 is for example, 10 to 50 times the amount of the compound of formula (III), as defined herein.

In particular, step b is carried out at a reaction temperature of from −10 deg C. to 40 deg C. In particular the crystallization is carried out at a temperature of from 0 to 40 deg C.

Typically, in step b) the molar ratio of the 2-acylamino-3-biphenyl propanoic acid compound of formula (III), as defined herein, to the compound of formula (V), (Va) or (Vb) as defined herein, is 1.0:(0.5 to 3.0).

Step c:

In a further embodiment, the present invention relates to a method for preparing a chiral compound of formula (I), or salt thereof,

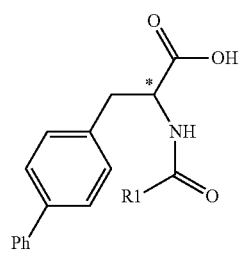
(I)

wherein

R1 is $C_{1-7}$alkyl, such as methyl or ethyl; or is substituted or unsubstituted $C_{6-10}$aryl, such as phenyl or para-chlorophenyl; and "*" means a chiral center with absolute stereochemistry (R) or (S), comprising treating a chiral compound of formula (II),

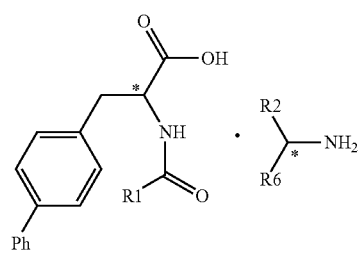
(II)

wherein

R1 is $C_{1-7}$alkyl, such as methyl or ethyl; or is substituted or unsubstituted $C_{6-10}$aryl, such as phenyl or para-chlorophenyl;

R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl;

R6 is $C_{6-10}$aryl, such as phenyl, and

"*" means a chiral center with absolute stereochemistry (R) or (S), with an acidic reagent to provide the compound of formula (I).

In a still further embodiment, the present invention relates to a method for preparing a compound of formula (Ia), or salt thereof,

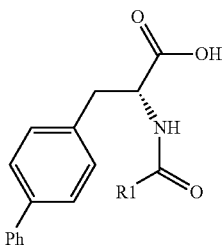
(Ia)

wherein

R1 is $C_{1-7}$alkyl, such as methyl or ethyl; or is substituted or unsubstituted $C_{6-10}$aryl, such as phenyl or para-chlorophenyl;

comprising treating a compound of formula (IIa),

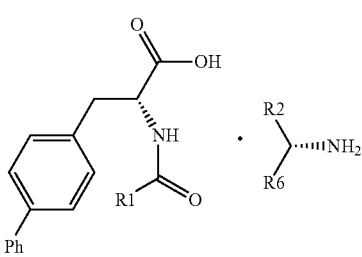
(IIa)

wherein

R1 is $C_{1-7}$alkyl, such as methyl or ethyl; or is substituted or unsubstituted $C_{6-10}$aryl, such as phenyl or para-chlorophenyl;

R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl, and R6 is $C_{6-10}$aryl, such as phenyl;

with an acidic reagent to provide the compound of formula (I).

In a still further embodiment, the present invention relates to a method for preparing a compound of formula (Ib), or salt thereof,

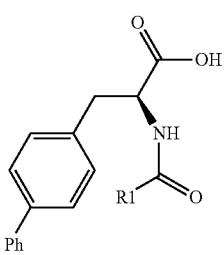
(Ib)

wherein
R1 is $C_{1-7}$alkyl, such as methyl or ethyl; or is substituted or unsubstituted $C_{6-10}$aryl, such as phenyl or para-chlorophenyl;
comprising
treating a compound of formula (IIb),

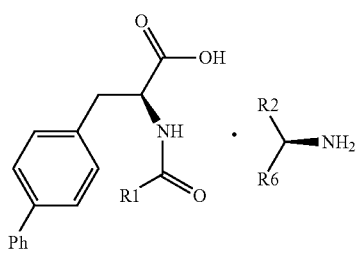

(IIb)

wherein
R1 is $C_{1-7}$alkyl, such as methyl or ethyl; or is substituted or unsubstituted $C_{6-10}$aryl, such as phenyl or para-chlorophenyl;
R2 is $C_{1-7}$alkyl, such as methyl; or is R3R4NC(=O)— or R5OC(=O)—, wherein R3 and R4 are independently selected from hydrogen or $C_{1-7}$alkyl; and R5 is $C_{1-7}$alkyl, and R6 is $C_{6-10}$aryl, such as phenyl;
with an acidic reagent
to provide the compound of formula (Ib).

Typically, the acidic reagent is an inorganic acid or an organic acid, such as hydrochloric acid, sulfuric acid, phosphoric acid, oxalic acid, citric acid, formic acid or acetic acid.

Typically, step c) is carried out in solvents generally known in the art, for example, a solvent, (named solvent 3), selected from water, methanol, ethanol, isopropanol and tetrahydrofuran. The amount of said solvent 3 is, for example, 2 to 20 times the feed amount (by weight) of the compound of formula II, as defined herein.

In particular, step c is carried out at a reaction temperature of from 10 deg C. to 95 deg C.

In one embodiment, the reaction time for step c) is of from 10 min to 5 hours.

Typically, in step c) the molar ratio of the compound of formula (II), as defined herein, to the acidic reagent is 1.0:(1.0 to 4.0).

Further Embodiments

In a further aspect, the present invention relates to a method for preparing a compound of formula (I), (Ia) or (Ib), as defined herein, or salt thereof, comprising
  i) step a), as described above;
  ii) step b), as described above; and
  iii) step c) as described above.

In a still further aspect, the present invention relates to a method for preparing a compound of formula (I), (Ia) or (Ib), as defined herein, or salt thereof, comprising
  iv) step b), as described above; and
  v) step c) as described above.

PREFERRED EMBODIMENTS

Embodiment 1

A process for preparing and resolving a 2-acylamino-3-biphenyl propanoic acid compound of formula III, which is characterized in that it is comprised of the following steps:

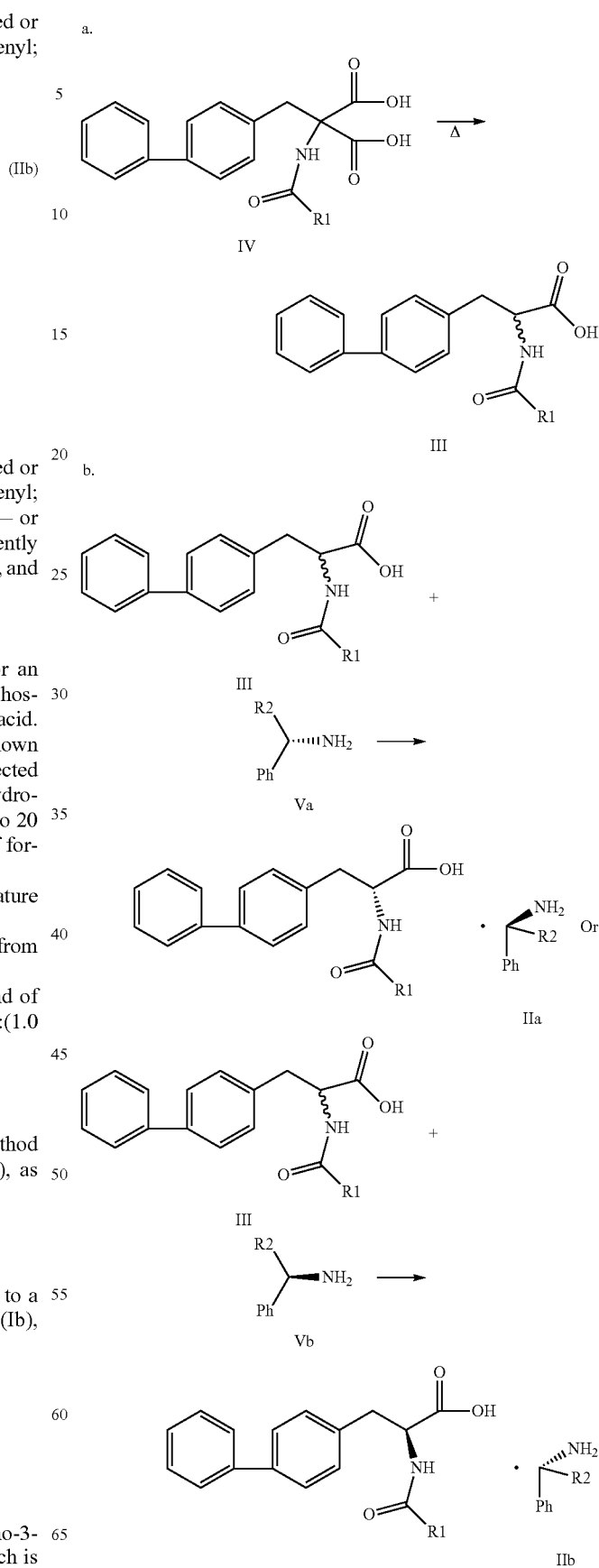

-continued c.

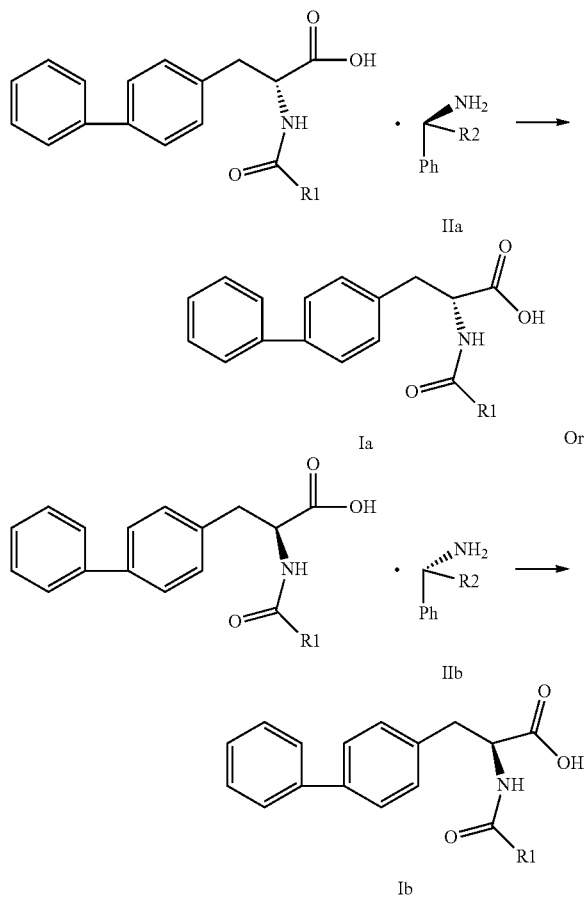

wherein
R1 is an alkyl group, a phenyl, or phenyl containing substituting group;
R2 is methyl or a group featuring the following structure:

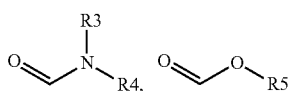

wherein R3, R4 are H or an alkyl group; and
R5 is an alkyl group.

Embodiment 2

A process for preparing and resolving the 2-acylamino-3-biphenyl propanoic acid compound according to embodiment 1, which is characterized in that said alkyl is preferably methyl, ethyl, propyl or isopropyl; said phenyl containing substituting group is preferably para-chlorophenyl.

Embodiment 3

A process for preparing and resolving the 2-acylamino-3-biphenyl propanoic acid compound according to embodiment 1 or 2, which is characterized in that step a is carried out by heating to a temperature of from 80 deg C. to 250 deg C.

Embodiment 4

A process for preparing and resolving the 2-acylamino-3-biphenyl propanoic acid compound according to embodiment 1 or 2, which is characterized in that during step a, the compound of formula IV reacts at reflux temperature a in solvent 1 to provide said 2-acylamino-3-biphenyl propanoic acid compound.

Embodiment 5

A process for preparing and resolving the 2-acylamino-3-biphenyl propanoic acid compound according to embodiment 4, which is characterized in that said solvent 1 is selected from water, toluene, xylene, ethylbenzene, chlorobenzene, dichlorobenzene, nitrobenzene, N,N-dimethyl formamide and 1-methyl-2-pyrrolidone.

Embodiment 6

A process for preparing and resolving the 2-acylamino-3-biphenyl propanoic acid compound according to embodiment 1, which is characterized in that during step b said 2-acylamino-3-biphenyl propanoic acid compound is reacted with a compound of formula Va or Vb in solvent 2 to obtain the crude wet compound of formula IIa or IIb.

Embodiment 7

A process for preparing and resolving the 2-acylamino-3-biphenyl propanoic acid compound according to embodiment 1, which is characterized in that during step b, said 2-acylamino-3-biphenyl propanoic acid compound reacts with a compound of formula Va or Vb in solvent 2 at a specific temperature to obtain the crude wet compound of formula IIa or IIb.

Embodiment 8

A process for preparing and resolving the 2-acylamino-3-biphenyl propanoic acid according to embodiment 7, which is characterized in that the said reaction takes place at a temperature of from −10 deg C. to 40 deg C.

Embodiment 9

A process for preparing and resolving the 2-acylamino-3-biphenyl propanoic acid compound according to embodiment 7, which is characterized in that the crude wet compound of formula IIa or IIb is added with solvent 2 to make it crystallize at a specific temperature and obtain the solid compound of formula IIa or IIb.

Embodiment 10

A process for preparing and resolving the 2-acylamino-3-biphenyl propanoic acid compound according to embodiment 9, characterized in that the said crystallization takes place at a temperature of from 0 deg C. to 40 deg C.

Embodiment 11

A process for preparing and resolving the 2-acylamino-3-biphenyl propanoic acid compound according to any one of embodiments 6, 7, 8, 9 or 10, which is characterized in that said solvent 2 can be methanol, ethanol, isopropanol, or their respective aqueous solutions.

Embodiment 12

A process for preparing and resolving the 2-acylamino-3-biphenyl propanoic acid compound according to embodiments 1 or 2, which is characterized in that during step b, the molar ratio of the 2-acylamino-3-biphenyl propanoic acid compound to the compound of formula Va or Vb is 1.0:(0.5 to 3.0).

Embodiment 13

A process for preparing and resolving the 2-acylamino-3-biphenyl propanoic acid compound according to embodiments 1 or 2, which is characterized in that the step c is carried out by adding an acidic reagent to obtain the compound of formula Ia or Ib.

Embodiment 14

A process for preparing and resolving the 2-acylamino-3-biphenyl propanoic acid compound according to embodiment 13, which is characterized in that the acidic reagent is selected from hydrochloric acid, sulphuric acid, phosphoric acid, oxalic acid, citric acid, formic acid and acetic acid.

Embodiment 15

A process for preparing and resolving the 2-acylamino-3-biphenyl propanoic acid compound according to embodiment 14, which is characterized in that the molar ratio of the compound of formula IIa or IIb to the acidic reagent is 1.0:(1.0 to 4.0).

General Terms:

Listed below are definitions of various terms used to describe the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

Alkyl being a radical or part of a radical is a straight or branched (one or, if desired and possible, more times) carbon chain, and is especially $C_1$-$C_7$-alkyl, such as $C_1$-$C_4$-alkyl, in particular branched $C_1$-$C_4$-alkyl, such as isopropyl. The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, such as methyl, ethyl, n-propyl, sec-propyl, n-butyl, isobutyl, sec-butyl, tert-butyl, in particular methyl, ethyl, n-propyl, isopropyl, n-butyl, isobutyl, sec-butyl, tert-butyl. In particular, $C_1$-$C_7$-alkyl is methyl, ethyl, propyl, or isopropyl. In one embodiment $C_1$-$C_7$-alkyl is methyl or ethyl.

Aryl, as a radical or part of a radical, for example is a mono- or bicyclic aryl with 6 to 22 carbon atoms, such as phenyl, indenyl, indanyl or naphthyl, in particular phenyl. Substituted $C_{6-10}$aryl is, for example, $C_{6-10}$aryl substituted by one or more substituents (for example one to three substituents) independently selected from, for example, $C_1$-$C_7$-alkyl, $C_1$-$C_7$-alkoxy-$C_1$-$C_7$-alkyl, $C_1$-$C_7$-alkoxy and halo. In one embodiment, substituted $C_{6-10}$aryl is $C_{6-10}$aryl substituted by halo, such as para-chlorophenyl.

Alkoxy, as a radical or part of a radical, is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Halo or halogen is preferably fluoro, chloro, bromo or iodo, most preferably chloro.

In the formulae of the present application the term

" ╱ "

on a C-sp³ indicates the absolute stereochemistry, either (R) or (S).

In the formulae of the present application the term

" ⟋ "

on a C-sp³ indicates the absolute stereochemistry, either (R) or (S).

In the formulae of the present application the term "∿∿∿" on a C-sp³ represents a racemic mixture, thus it means a chiral center wherein the (S) stereoisomer and the (R) stereoisomer are in a 50:50 ratio.

In the formulae of the present application the term "Ph" means phenyl.

The term "chiral", as used herein, refers to molecules which have the property of non-superimposability on their mirror image partner, while the term "achiral" refers to molecules which are superimposable on their mirror image partner. Any possible pure enantiomer or mixture of enantiomers, pure diastereoisomer or mixture of diasteromer are encompassed by the present invention. In one embodiment the term chiral refers to an entiomerically enriched mixture of enantiomers. The term "enantiomerically enriched", as used herein, refers to a mixture of enantiomers wherein the amount of one enantiomer is higher than 50%. In another embodiment the term chiral refers to a diasteromerically enriched mixture of diasteromers. The term "diasteromerically enriched", as used herein, refers to a mixture of diasteromers wherein the amount of one diasteromer is higher than 50%.

In a further embodiment the term chiral, as used herein, refers to a "diastereomeric mixture", in particular, a mixture of diastereoisomers (R,R*) and (S,R*) or (R,S*) and (S,S*), wherein R and S refer to the absolute configuration of the asymmetric carbon of a carboxyl group containing molecule and R* and S* refer to the absolute configuration of the asymmetric carbon of an amine containing molecule. A compound of formula (II) may thus be a diasteromeric mixture as defined herein.

The term "crystallization", as used herein, refers to a process by which a single diastereoisomer is preferentially crystallized out from a diastereoisomeric mixture, as defined herein. Thus, crystallization refers, in one embodiment, to the process of preferentially crystallizing out the diastereoisomer (R,R*) or (S,R*) from the mixture (R,R*) and (S,R*), as defined above. In another embodiment, crystallization refers to the process of preferentially crystallizing out the diastereoisomer (R,S*) or (S,S*) from the mixture (R,S*) and (S,S*), as defined above.

The term "resolving", as employed herein, refers to converting a 50:50 mixture of diastereoisomers (R,R*) and (S,R*) or (R,S*) and (S,S*), as defined above, in a mixture enriched in either one of the diastereoisomers. An enriched mixture is thus one that contains a higher abundance or proportion of one diastereoisomer over the other.

The term "reflux" refers to the temperature at which the reaction mixture boils, preferably a temperature up to 180° C., preferably up to 140° C.

As used herein, the term "room temperature" or "ambient temperature" means a temperature of from 20 to 35° C., such as of from 20 to 25° C.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, is to be understood as referring also to one or more salts thereof or a mixture of a corresponding free compound, intermediate or starting material and one or more salts thereof, each of which is intended to include also any solvate, metabolic precursor such as ester or amide, or salt of any one or more of these, as appropriate and expedient and if not explicitly mentioned otherwise. Different crystal forms may be obtainable and then are also included. Salts can be formed where salt forming groups, such as basic or acidic groups, are present that can exist in dissociated form at least partially, e.g. in a pH range from 4 to 10 in aqueous solutions, or can be isolated especially in solid, especially crystalline, form. In the presence of basic groups (e.g. imino or amino), salts may be formed preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid. In the presence of negatively charged radicals, such as carboxy or sulfo, salts may be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine. When a basic group and an acid group are present in the same molecule, internal salts may also be formed. Particularly useful salts include the hydrochloric acid, hydrobromic acid, sulfuric acid, nitric acid, phosphoric, lactic acid, fumaric acid, succinic acid, oxalic acid, malic acid, malonic acid, tartaric acid, tolyltartaric acid, benzoyltartaric acid, orotic acid, nicotinic acid, methane-sulfonic acid or 4-methylbenzenesulfonic acid salts of compounds of formula (I), (III) or (IV) and the like formed from reaction with the above reagents. Methods to prepare acid addition salts are described in the literature, for example, in the relevant chapters of "CRC Handbook of Optical Resolutions via Diasteromeric Salt Formation", D. Kozma, CRC Press 2002, in Acta Cryst, 2006, B62, 498-505 and in Synthesis, 2003, 13, 1965-1967.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Particular embodiments of the invention are provided in the following Examples. These Examples serve to illustrate the invention without limiting the scope thereof, while they on the other hand represent preferred embodiments of the reaction steps, intermediates and/or the process of the present invention.

Example 1

Preparation of 2-acetylamino-3-biphenyl propanoic acid

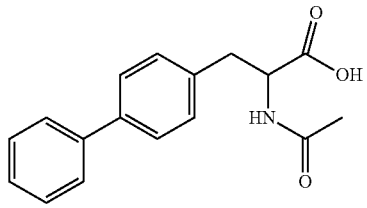 [SMILES: CC(=O)NC(Cc1ccc(-c2ccccc2)cc1)C(=O)O]

In a dry and clean reaction bottle, add 40 g of 2-acetylamino-2-(4-phenyl benzyl) malonic acid. Add 1000 ml of water and maintain at reflux temperature for 48 hours. Test for completion of reaction with HPLC. Cool down to room temperature and vacuum filtrate it. Dry in an oven at 90 to 100 deg C. and normal pressure. After drying, obtain 31.1 g of 2-acetylamino-3-biphenyl propanoic acid. Yield ratio: 89.9%. 1H NMR (500 MHz, DMSO-d6): 1.82, 2.89-2.93, 3.08-3.12, 4.45-4.50, 7.33-7.37, 7.44-7.47, 7.58-7.60, 7.64-7.66, 8.26~8.28, 12.75; MS (m/z): 224.07 (100), 167.14 (56), 165.16 (26), 282.94 ([MH+], 1).

Example 2

Preparation of 2-(N-para-chlorobenzoyl)amino-3-biphenyl propanoic acid

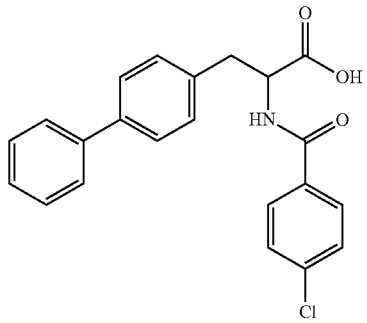 [SMILES: O=C(NC(Cc1ccc(-c2ccccc2)cc1)C(=O)O)c1ccc(Cl)cc1]

Take 20 g of 2-(N-para-chlorobenzoyl)amino-2-(4-phenyl benzyl) malonic acid, and place in a drying oven at 105 deg C. and normal pressure for 12 hours. Test for completion of reaction with HPLC. Obtain 16.4 g of the dry product, 2-(N-para-chlorobenzoyl)amino-3-biphenyl propanoic acid. Yield ratio: 94.8%. 1H NMR (500 MHz, DMSO-d6): 3.12-3.17, 3.25-3.29, 4.66-4.71, 7.32-7.35, 7.42-7.45, 7.54-7.57, 7.58-7.60, 7.62-7.64, 7.86-7.88, 8.89-8.91, 12.963; MS (m/z): 224.0 (100), 167.1 (55), 165.1 (21), 139.1 (10), 111.1 (5), 378.8 ([MH+], 1).

Example 3

Preparation of 2-acetylamino-3-biphenyl propanoic acid

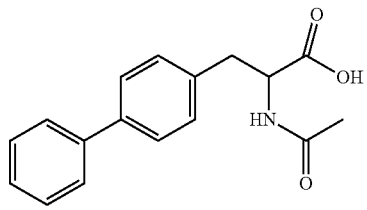 [SMILES: CC(=O)NC(Cc1ccc(-c2ccccc2)cc1)C(=O)O]

In a dry and clean reaction bottle, add 20 g of 2-acetylamino-2-(4-phenyl benzyl) malonic acid. Add 100 ml of xylene and maintain at reflux temperature for 3 hours. Test for completion of reaction with HPLC. Cool down to room temperature and vacuum filtrate it. Dry in an oven at 90 to 100 deg C. and normal pressure. After drying, obtain 15.6 g of 2-acetylamino-3-biphenyl propanoic acid. Yield ratio: 90.2%. Spectroscopic data as Example 1.

Example 4

Preparation of 2-(N-formyl phenyl)amino-3-biphenyl propanoic acid

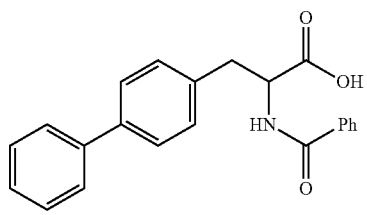 [SMILES: O=C(NC(Cc1ccc(-c2ccccc2)cc1)C(=O)O)c1ccccc1]

In a clean and dry reaction bottle, add 40 g of 2-(N-formyl phenyl)amino-2 (phenyl benzyl) malonic acid. Add 2100 ml of N,N-dimethyl formamide (DMF) and maintain at reflux temperature for 40 hours. Test for completion of reaction with HPLC. Cool down to room temperature and vacuum filtrate it. Dry in an oven at 90 to 100 deg C. and normal pressure. After drying, obtain 32.8 g of 2-(N-formyl phenyl)amino-3-biphenyl propanoic acid. Yield ratio: 92.8%. 1H NMR (500 MHz, DMSO-d6): 3.12-3.17, 3.23-3.27, 4.65-4.70, 7.31-7.33, 7.34-7.45, 7.46-7.48, 7.58-7.60, 7.62-7.64, 7.83-7.84, 8.77-8.79, 12.85; MS (m/z): 224.0 (100), 167.1 (34), 165.1 (15), 105.1 (10), 77.2 (18), 344.8 ([MH+], 1).

Example 5

Preparation of 2-(N-isopropyl formyl)amino-3-biphenyl propanoic acid

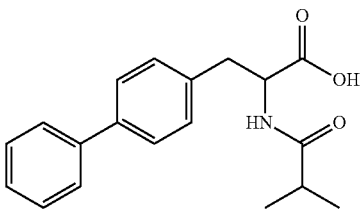 [SMILES: CC(C)C(=O)NC(Cc1ccc(-c2ccccc2)cc1)C(=O)O]

In a clean and dry reaction bottle, add 20 g of (2-(N-isopropyl formyl)amino-2 (phenyl benzyl) malonic acid. Add 200 ml of 1,3-dichlorobenzene, heat to reflux temperature and maintain temperature for 25 hours. Test for completion of reaction with HPLC. Cool down to room temperature and vacuum filtrate it. Dry in an oven at 90 to 100 deg C. and normal pressure. After drying, obtain 16.3 g of 2-(N-isopropyl formyl)amino-3-biphenyl propanoic acid. Yield ratio: 94.2%. 1H NMR (500 MHz, DMSO-d6): 0.87-0.88, 2.37-2.43, 2.89-2.94, 3.09-3.13, 4.44-4.48, 7.31-7.36, 7.43-7.46, 7.57-7.59, 7.63-7.65, 8.01-8.08, 12.71; MS (m/z): 224.0 (100), 167.1 (38), 165.2 (16), 310.9 ([MH+], 1).

Example 6

Preparation of 2-propionyl amino-3-biphenyl propanoic acid

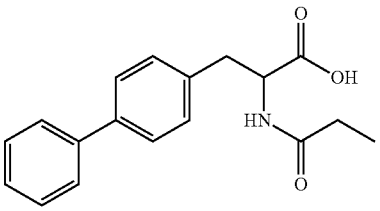 [SMILES: CCC(=O)NC(Cc1ccc(-c2ccccc2)cc1)C(=O)O]

In a dry and clean reaction bottle, add 20 g of 2-propionyl amino-2-(4-benzyphenyl) malonic acid. Add 100 ml of nitrobenzene, heat to reflux temperature, and maintain temperature for 2 hours. Test for completion of reaction with HPLC. Cool down to room temperature and vacuum filtrate it. Dry in an oven at 90 to 100 deg C. and normal pressure. After drying, obtain 15.8 g of 2-propionyl amino-3-biphenyl propanoic acid. Yield ratio: 92.1%. 1H NMR (500 MHz, DMSO-d6): 0.93, 2.06-2.11, 2.88-2.93, 3.08-3.12, 4.44-4.49, 7.32-7.36, 7.44-7.47, 7.58-7.59, 7.64-7.66, 8.15-8.16, 12.72; MS (m/z): 224.0 (100), 167.1 (45), 165.1 (20), 296.9 ([MH+], 1).

Example 7

Preparation of 2-butyryl amino-3-biphenyl propanoic acid

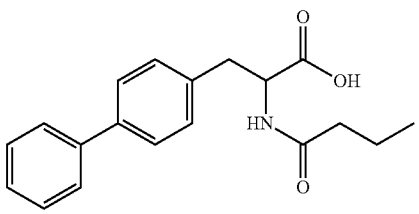 [SMILES: CCCC(=O)NC(Cc1ccc(-c2ccccc2)cc1)C(=O)O]

In a dry and clean reaction bottle, add 20 g of 2-butyryl amino-2-(4-benzyphenyl) malonic acid. Add 100 ml of 1-methyl-2-pyrrolidone (NMP), heat to reflux temperature, maintain temperature for 15 hours. Test for completion of reaction with HPLC. Cool down to room temperature and vacuum filtrate it. Dry in an oven at 90 to 100 deg C. and normal pressure. After drying, obtain 16.0 g of 2-butyryl amino-3-biphenyl propanoic acid. Yield ratio: 93.5%. 1H NMR (500 MHz, DMSO-d6): 0.74-0.77, 1.42-1.46, 2.03-2.06, 2.87-2.92, 3.09-3.12, 4.46-4.51, 7.32-7.36, 7.43-7.47, 7.56-7.59, 7.63-7.65, 8.16-8.18, 12.70; MS (m/z): 224.0 (100), 167.1 (39), 165.2 (16), 310.9 ([MH+], 1).

Example 8

Preparation of 2-acetylamino-3-biphenyl propanoic acid

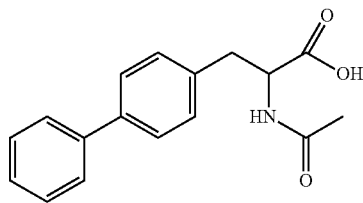 [SMILES: CC(=O)NC(Cc1ccc(-c2ccccc2)cc1)C(=O)O]

In a dry and clean reaction bottle, add 40 g of 2-acetylamino-2-(4-benzyphenyl) malonic acid. Add 5 ml of ethylbenzene and maintain temperature at 80 deg C. for 48 hours. Test for completion of reaction with HPLC. Cool down to room temperature and vacuum filtrate it. Dry in an oven at 90 to 100 deg C. and normal pressure. After drying, obtain 30.5 g of 2-acetylamino-3-biphenyl propanoic acid. Yield ratio: 87.6%. Spectroscopic data as Example 1.

Example 9

Preparation of 2-butyryl amino-3-biphenyl propanoic acid

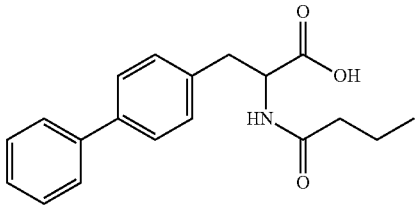 [SMILES: CCCC(=O)NC(Cc1ccc(-c2ccccc2)cc1)C(=O)O]

Take 20 g of 2-butyryl amino-2-(4-phenyl benzyl) malonic acid, and place in a drying oven at 165 deg C. and normal pressure for 18 hours. Test for completion of reaction with HPLC. Obtain 14.3 g of dry product of 2-butyryl amino-3-biphenyl propanoic acid. Yield ratio: 90.3%. Spectroscopic data as Example 7.

Example 10

Preparation of 2-(N-formyl phenyl)amino-3-biphenyl propanoic acid

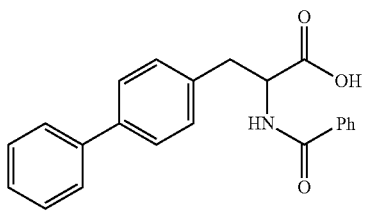 [SMILES: O=C(NC(Cc1ccc(-c2ccccc2)cc1)C(=O)O)c1ccccc1]

Take 20 g of 2-(N-formyl phenyl)amino-2-(4-phenyl benzyl) malonic acid, and place in a drying oven at 80 deg C. and normal pressure for 12 hours. Test for completion of reaction with HPLC. Obtain 12.7 g of the product, 2-(N-formyl phenyl)amino-3-biphenyl propanoic acid. Yield ratio: 91.7%. Spectroscopic data as Example 4.

Example 11

Preparation of 2-propionyl amino-3-biphenyl propanoic acid

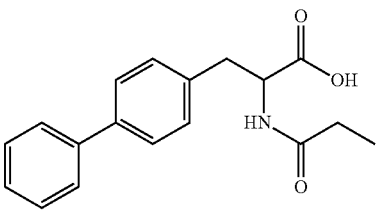 [SMILES: CCC(=O)NC(Cc1ccc(-c2ccccc2)cc1)C(=O)O]

Take 20 g of 2-propionyl amino-2-(4-phenyl benzyl) malonic acid, and place in a drying oven at 250 deg C. and normal pressure for 12 hours. Test for completion of reaction with HPLC. Obtain 15.4 g of dry product of 2-propionyl amino-3-biphenyl propanoic acid. Yield ratio: 89.8%. Spectroscopic data as Example 6.

The products from the examples above (1~11) are used as reactants in the subsequent reaction step (step b).

Example 12

Preparation of (D)-2-acetylamino-3-biphenyl propanoic acid-(S)-1-phenethylamine salt In a dry and clean reaction bottle, add 300 ml of ethanol and 10 g of 2-acetylamino-3-biphenyl propanoic acid. Heat to increase temperature and dissolve the compound. Add 4 g of S-1-phenethylamine. Slowly cool down to 10 deg C. Maintain temperature for 0.5 hours. Vacuum filtrate it. Obtain crude wet product of (D)-2-acetylamino-3-biphenyl propanoic acid-(S)-1-phenethylamine salt.

Then, add the crude wet product of (D)-2-acetylamino-3-biphenyl propanoic acid-(S)-1-phenethylamine salt to a dry and clean reaction bottle. Add 100 ml of ethanol. Heat to increase temperature to reflux. Slowly cool down to 0 deg C. Vacuum filtrate it. Dry in a drying oven for 8 hours at 50 to 60 deg C. Obtain 5.7 g of the product. Yield ratio: 39.9%.

Example 13

Preparation of (D)-2-acetylamino-3-biphenyl propanoic acid-(S)-1-phenethylamine salt In a dry and clean reaction bottle, add 300 ml of methanol and 10 g of 2-acetylamino-3-biphenyl propanoic acid. Heat to increase temperature and dissolve the compound. Add 3 g of S-1-phenethylamine. Slowly cool down to 30 deg C. Maintain temperature for 0.5 hours. Vacuum filtrate it. Obtain crude wet product of (D)-2-acetylamino-3-biphenyl propanoic acid-(S)-1-phenethylamine salt.

Then, add the crude wet product of (D)-2-acetylamino-3-biphenyl propanoic acid-(S)-1-phenethylamine salt to a dry and clean reaction bottle. Add 100 ml of methanol. Heat to increase temperature to reflux. Slowly cool down to 30 deg C. Vacuum filtrate it. Dry in a drying oven for 8 hours at 50 to 60 deg C. Obtain 5.5 g of the product. Yield ratio: 38.5%.

Example 14

Preparation of (D)-2-acetylamino-3-biphenyl propanoic acid-(S)-1-phenethylamine salt In a dry and clean reaction bottle, add 300 ml of ethanol, 30 ml of tap water, and 10 g of 2-acetylamino-3-biphenyl propanoic acid. Heat to increase temperature and dissolve the compound. Add 3 g of S-1-phenethylamine. Slowly cool down to 35 deg C. Maintain temperature for 1 hours. Vacuum filtrate it. Obtain crude wet product of (D)-2-acetylamino-3-biphenyl propanoic acid-(S)-1-phenethylamine salt.

Then, add the crude wet product of (D)-2-acetylamino-3-biphenyl propanoic acid-(S)-1-phenethylamine salt to a dry and clean reaction bottle. Add 100 ml of ethanol. Heat to increase temperature to reflux. Slowly cool down to 35 deg C. Vacuum filtrate it. Dry in a drying oven for 8 hours at 50 to 60 deg C. Obtain 5.8 g of the product. Yield ratio: 40.6%.

Example 15

Preparation of (L)-2-acetylamino-3-biphenyl propanoic acid-(R)-1-phenethylamine salt In a dry and clean reaction bottle, add 634 ml of ethanol and 10 g of 2-acetylamino-3-biphenyl propanoic acid. Heat to increase temperature and dissolve the compound. Add 12.7 g of R-1-phenethylamine. Slowly cool down to 15 deg C. Maintain temperature for 0.5 hours. Vacuum filtrate it. Obtain crude wet product of (L)-2-acetylamino-3-biphenyl propanoic acid-(R)-1-phenethylamine salt.

Then, add the crude wet product of (L)-2-acetylamino-3-biphenyl propanoic acid-(R)-1-phenethylamine salt to a dry and clean reaction bottle. Add 200 ml of methanol. Heat to increase temperature to reflux. Slowly cool down to 20 deg C. Vacuum filtrate it. Dry in a drying oven for 8 hours at 50 to 60 deg C. Obtain 6.0 g of the product. Yield ratio: 42.0%.

Example 16

Preparation of (D)-2-acetylamino-3-biphenyl propanoic acid-(S)-2-amino-2-phenyl acetamide salt In a dry and clean reaction bottle, add 380 ml of methanol and 10 g of 2-acetylamino-3-biphenyl propanoic acid. Heat to increase temperature and dissolve the compound. Add 9.2 g of S-2-amino 2-phenyl acetamide. Slowly cool down to 40 deg C. Maintain temperature for 0.5 hours. Vacuum filtrate it. Obtain crude wet product of (D)-2-acetylamino-3-biphenyl propanoic acid-(S)-2-amino 2-phenyl acetamide salt.

Then, add the crude wet product of (D)-2-acetylamino-3-biphenyl propanoic acid-(S)-2-amino 2-phenyl acetamide salt to a dry and clean reaction bottle. Add 100 ml of ethanol. Heat to increase temperature to reflux. Slowly cool down to 30 deg C. Vacuum filtrate it. Dry in a drying oven for 8 hours at 50 to 60 deg C. Obtain 5.7 g of the product. Yield ratio: 39.8%.

Example 17

Preparation of (L)-2-acetylamino-3-biphenyl propanoic acid-(R)-2-amino N-methyl 2-phenyl acetamide salt In a dry and clean reaction bottle, add 127 ml of isopropanol, and 10 g of 2-acetylamino-3-biphenyl propanoic acid. Heat to increase temperature and dissolve the compound. Add 2.9 g of R-2-amino N-methyl 2-phenyl acetamide. Slowly cool down to −10 deg C. Maintain temperature for 1 hour. Vacuum filtrate it. Obtain crude wet product of (L)-2-acetylamino-3-biphenyl propanoic acid-(R)-2-amino N-methyl 2-phenyl acetamide salt.

Then, add the crude wet product of (L)-2-acetylamino-3-biphenyl propanoic acid-(R)-2-amino N-methyl 2-phenyl acetamide salt to a dry and clean reaction bottle. Add 100 ml of ethanol. Heat to increase temperature to reflux. Slowly cool down to 40 deg C. Vacuum filtrate it. Dry in a drying oven for 8 hours at 50 to 60 deg C. Obtain 6.1 g of the product. Yield ratio: 42.7%.

Example 18

Preparation of (L)-2-acetylamino-3-biphenyl propanoic acid-(R)-2-amino N,N-dimethyl-2-phenyl acetamide salt In a dry and clean reaction bottle, add 400 ml of ethanol and 10 g of 2-acetylamino-3-biphenyl propanoic acid. Heat to increase temperature and dissolve the compound. Add 5 g of R-2-amino N,N-dimethyl-2-phenyl acetamide. Slowly cool down to 25 deg C. Maintain temperature for 0.5 hours. Vacuum filtrate it. Obtain crude wet product of (L)-2-acetylamino-3-biphenyl propanoic acid-(R)-2-amino N,N-dimethyl-2-phenyl acetamide salt.

Then, add the crude wet product of (L)-2-acetylamino-3-biphenyl propanoic acid-(R)-2-amino N,N-dimethyl-2-phenyl acetamide salt to a dry and clean reaction bottle. Add 100 ml of ethanol. Heat to increase temperature to reflux. Slowly cool down to 0 deg C. Vacuum filtrate it. Dry in a drying oven for 8 hours at 50 to 60 deg C. Obtain 4.9 g of the product. Yield ratio: 38.7%.

Example 19

Preparation of (D)-2-acetylamino-3-biphenyl propanoic acid-(S)-amino-phenyl-ethyl acetate amine salt In a dry and clean reaction bottle, add 300 ml of isopropanol, 100 ml of tap water, and 10 g of 2-acetylamino-3-biphenyl propanoic acid. Heat to increase temperature and dissolve the compound. Add 3.5 g of S-amino-phenyl-acetic ether. Slowly cool down to 0 deg C. Maintain temperature for 0.5 hours. Vacuum filtrate it. Obtain crude wet product of (D)-2-acetylamino-3-biphenyl propanoic acid-(S)-amino-phenyl-ethyl acetate amine salt.

Then, add the crude wet product of (D)-2-acetylamino-3-biphenyl propanoic acid-(S)-amino-phenyl-ethyl acetate amine salt to a dry and clean reaction bottle. Add 100 ml of methanol. Heat to increase temperature to reflux. Slowly cool down to 30 deg C. Vacuum filtrate it. Dry in a drying oven for 8 h at 50 to 60 deg C. Obtain 5.6 g of the product. Yield ratio: 39.0%.

Example 20

Preparation of (D)-2-acetylamino-3-biphenyl propanoic acid-(S)-amino-phenyl-methyl acetate amine salt In a dry and clean reaction bottle, add 300 ml of methanol, 30 ml of tap water, and 10 g of 2-acetylamino-3-biphenyl propanoic acid. Heat to increase temperature and dissolve the compound. Add 10 g of S-amino-phenyl-methyl acetate. Slowly cool down to −5 deg C. Maintain temperature for 1 hours. Vacuum filtrate it. Obtain crude wet product of (D)-2-acetylamino-3-biphenyl propanoic acid-(S)-amino-phenyl-methyl acetate amine salt.

Then, add the crude wet product of (D)-2-acetylamino-3-biphenyl propanoic acid-(S)-amino-phenyl-methyl acetate amine salt to a dry and clean reaction bottle. Add 100 ml of ethanol. Heat to increase temperature to reflux. Slowly cool down to 35 deg C. Vacuum filtrate it. Dry in a drying oven for 8 hours at 50 to 60 deg C. Obtain 6.0 g of the product. Yield ratio: 41.5%.

Example 21

Preparation of (L)-2-acetylamino-3-biphenyl propanoic acid-(R)-amino-phenyl-isopropyl acetate amine salt In a dry and clean reaction bottle, add 300 ml of ethanol and 10 g of 2-acetylamino-3-biphenyl propanoic acid. Heat to increase temperature and dissolve the compound. Add 15 g of R-amino-phenyl-isopropyl acetate amine. Slowly cool down to 20 deg C. Maintain temperature for 0.5 hours. Vacuum filtrate it. Obtain crude wet product of (L)-2-acetylamino-3-biphenyl propanoic acid-(R)-amino-phenyl-isopropyl acetate amine salt.

Then, add the crude wet product of (L)-2-acetylamino-3-biphenyl propanoic acid-(R)-amino-phenyl-isopropyl acetate amine salt to a dry and clean reaction bottle. Add 100 ml of ethanol. Heat to increase temperature to reflux. Slowly cool down to 20 deg C. Vacuum filtrate it. Dry in a drying oven for 8 hours at 50 to 60 deg C. Obtain 5.2 g of the product. Yield ratio: 36.5%.

Example 22

Preparation of (L)-2-propionyl amino-3-biphenyl propanoic acid-(R)-2-amino N,N-dimethyl-2-phenyl-acetamide salt In a dry and clean reaction bottle, add 400 ml of ethanol and 10 g of 2-propionyl amino-3-biphenyl propanoic acid. Heat to increase temperature and dissolve the compound. Add 5 g of R-2-amino N,N-dimethyl-2-phenyl acetamide. Slowly cool down to 25 deg C. Maintain temperature for 0.5 hours. Vacuum filtrate it. Obtain crude wet product of (L)-2-propionyl amino-3-biphenyl propanoic acid-(R)-2-amino N,N-dimethyl-2-phenyl-acetamide salt.

Then, add the crude wet product of (L)-2-propionyl amino-3-biphenyl propanoic acid-(R)-2-amino N,N-dimethyl-2-phenyl-acetamide salt to a dry and clean reaction bottle. Add 100 ml of ethanol. Heat to increase temperature to reflux. Slowly cool down to 0 deg C. Vacuum filtrate it. Dry in a drying oven for 8 hours at 50 to 60 deg C. Obtain 4.8 g of the product. Yield ratio: 32.7%.

Example 23

Preparation of (D)-2-butyryl amino-3-biphenyl propanoic acid-(S)-amino-phenyl-ethyl acetate amine salt In a dry and clean reaction bottle, add 300 ml of isopropanol, 100 ml of tap water, and 10 g of 2-butyryl amino-3-biphenyl propanoic acid. Heat to increase temperature and dissolve the compound. Add 3.5 g of S-amino-phenyl-ethyl acetate. Slowly cool down to 0 deg C. Maintain temperature for 0.5 hours. Vacuum filtrate it. Obtain crude wet product of (D)-2-butyryl amino-3-biphenyl propanoic acid-(S)-amino-phenyl-ethyl acetate amine salt.

Then, add the crude wet product of (D)-2-butyryl amino-3-biphenyl propanoic acid-(S)-amino-phenyl-ethyl acetate amine salt to a dry and clean reaction bottle. Add 100 ml of methanol. Heat to increase temperature to reflux. Slowly cool down to 30 deg C. Vacuum filtrate it. Dry in a drying oven for 8 hours at 50 to 60 deg C. Obtain 4.3 g of the product. Yield ratio: 31.5%.

Example 24

Preparation of (D)-2-(N-formyl phenyl)amino-3-biphenyl propanoic acid-(S)-amino-phenyl-methyl acetate amine salt In a dry and clean reaction bottle, add 300 ml of methanol, 30 ml of tap water, and 10 g of 2-(N-formyl phenyl)amino-3-biphenyl propanoic acid. Heat to increase temperature and dissolve the compound. Add 10 g of S-amino-phenyl-methyl acetate. Slowly cool down to −5 deg C. Maintain temperature for 1 hour. Vacuum filtrate it. Obtain crude wet product of (D)-2-(N-formyl phenyl)amino-3-biphenyl propanoic acid-(S)-amino-phenyl-methyl acetate amine salt.

Then, add the crude wet product of (D)-2-(N-formyl phenyl)amino-3-biphenyl propanoic acid-(S)-amino-phenyl-methyl acetate amine salt to a dry and clean reaction bottle. Add 100 ml of ethanol. Heat to increase temperature to reflux. Slowly cool down to 35 deg C. Vacuum filtrate it. Dry in a drying oven for 8 hours at 50 to 60 deg C. Obtain 5.0 g of the product. Yield ratio: 38.6%.

Example 25

Preparation of (L)-2-(N-para-chlorobenzoyl)amino-3-biphenyl propanoic acid-(R)-amino-phenyl-isopropyl acetate amine salt In a dry and clean reaction bottle, add 300 ml of ethanol and 10 g of 2-(N-para-chlorobenzoyl)amino-3-biphenyl propanoic acid. Heat to increase temperature and dissolve the compound. Add 15 g of R-amino-phenyl-isopropyl acetate amine. Slowly cool down to 20 deg C. Maintain temperature for 0.5 hours. Vacuum filtrate it. Obtain crude wet product of (L)-2-(N-para-chlorobenzoyl)amino-3-biphenyl propanoic acid-(R)-amino-phenyl-isopropyl acetate amine salt.

Then, add the crude wet product of (L)-2-(N-para-chlorobenzoyl)amino-3-biphenyl propanoic acid-(R)-amino-phenyl-isopropyl acetate amine salt to a dry and clean reaction bottle. Add 100 ml of ethanol. Heat to increase temperature to reflux. Slowly cool down to 20 deg C. Vacuum filtrate it. Dry in a drying oven for 8 hours at 50 to 60 deg C. Obtain 4.5 g of the product. Yield ratio: 30.5%.

The products from the Examples above (12~25) are used as reactants in subsequential reaction step (step c).

Example 26

Preparation of (D)-2-acetylamino-3-biphenyl propanoic acid

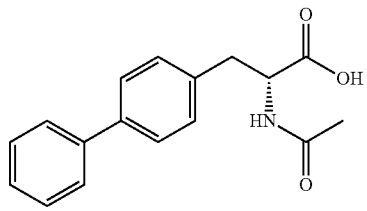 [SMILES: CC(=O)N[C@H](Cc1ccc(-c2ccccc2)cc1)C(=O)O]

In a dry and clean reaction bottle, add 200 ml of ethanol and 10 g of (D)-2-acetylamino-3-biphenyl propanoic acid-(S)-1-phenethylamine salt. Elevate temperature to 50 deg C. Instill 3.5 g of hydrochloric acid. Maintain temperature for 1 hour. Cool down to 0 to 5 deg C. Vacuum filtrate it. Obtain 6.5 g of the product (D)-2-acetylamino-3-biphenyl propanoic acid. Yield ratio: 93.7%. 1H NMR (500 MHz, DMSO-d6): 1.81, 2.87-2.92, 3.07-3.11, 4.43-4.48, 7.32-7.36, 7.44-7.47, 7.58-7.60, 7.64-7.66, 8.25-8.26, 12.74; MS (m/z): 224.0 (100), 167.1 (56), 165.2 (26), 282.9 ([MH+], 1).

Example 27

Preparation of (D)-2-acetylamino-3-biphenyl propanoic acid

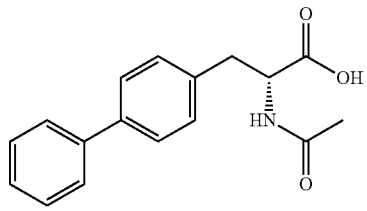 [SMILES: CC(=O)N[C@H](Cc1ccc(-c2ccccc2)cc1)C(=O)O]

In a dry and clean reaction bottle, add 100 ml of tap water and 10 g of (D)-2-acetylamino-3-biphenyl propanoic acid-(S)-1-phenethylamine salt. Elevate temperature to 60 deg C. Instill 2.5 g of sulfuric acid. Maintain temperature for 10 min. Slowly cool reaction solution down to 0 to 5 deg C. Vacuum filtrate it. Obtain 6.5 g of the product (D)-2-acetylamino-3-biphenyl propanoic acid. Yield ratio: 92.9%. Spectroscopic data as Example 26.

Example 28

Preparation of (L)-2-acetylamino-3-biphenyl propanoic acid

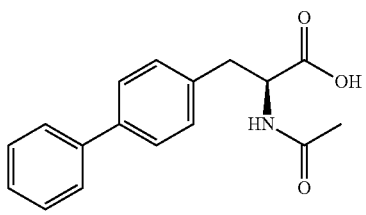 [SMILES: CC(=O)N[C@@H](Cc1ccc(-c2ccccc2)cc1)C(=O)O]

In a dry and clean reaction bottle, add 50 ml of tetrahydrofuran and 10 g of (L)-2-acetylamino-3-biphenyl propanoic acid-(R)-1-phenethylamine salt. Elevate temperature to 40 deg C. Instill 3.5 g of hydrochloric acid. Maintain temperature for 1 hour. Cool down to 10 to 20 deg C. Vacuum filtrate it. Obtain 6.4 g of the product (L)-2-acetylamino-3-biphenyl propanoic acid. Yield ratio: 91.4%. 1H NMR (500 MHz, DMSO-d6): 1.82, 2.88-2.93, 3.08-3.12, 4.45-4.50, 7.33-7.36, 7.44-7.47, 7.58-7.60, 7.65-7.66, 8.26-8.28, 12.76; MS (m/z): 224.0 (100), 167.1 (54), 165.1 (26), 282.9 ([MH+], 1).

Example 29

Preparation of (D)-2-acetylamino-3-biphenyl propanoic acid

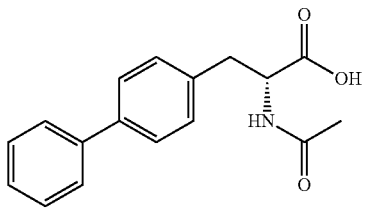 [SMILES: CC(=O)N[C@H](Cc1ccc(-c2ccccc2)cc1)C(=O)O]

In a dry and clean reaction bottle, add 253 ml of methanol and 10 g of (D)-2-acetylamino-3-biphenyl propanoic acid-(S)-1-phenethylamine salt. Elevate temperature to 95 deg C. Instill 9.8 g of phosphoric acid. Maintain temperature for 5 hours. Cool down to 0 to 5 deg C. Vacuum filtrate it. Obtain 6.3 g of the product (D)-2-acetylamino-3-biphenyl propanoic acid. Yield ratio: 90.7%. Spectroscopic data as Example 26.

Example 30

Preparation of (D)-2-acetylamino-3-biphenyl propanoic acid

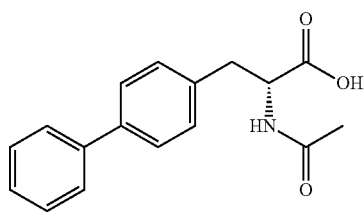 [SMILES: CC(=O)N[C@H](Cc1ccc(-c2ccccc2)cc1)C(=O)O]

In a dry and clean reaction bottle, add 25 ml of isopropanol and 10 g of (D)-2-acetylamino-3-biphenyl propanoic acid-(S)-1-phenethylamine salt. Elevate temperature to 10 deg C. Instill 4.5 g of oxalic acid. Maintain temperature for 10 min. Slowly cool reaction solution down to 0 to 5 deg C. Vacuum filtrate it. Obtain 6.7 g of the product (D)-2-acetylamino-3-biphenyl propanoic acid. Yield ratio: 95.7%. Spectroscopic data as Example 26.

Example 31

Preparation of (L)-2-acetylamino-3-biphenyl propanoic acid

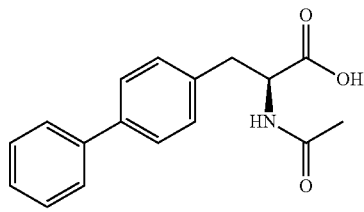

In a dry and clean reaction bottle, add 100 ml of tetrahydrofuran and 10 g of (L)-2-acetylamino-3-biphenyl propanoic acid-(R)-1-phenethylamine salt. Elevate temperature to 40 deg C. Instill 3.5 g of hydrochloric acid. Maintain temperature for 4 hours. Cool down to 10 to 20 deg C. Vacuum filtrate it. Obtain 6.6 g of the product (L)-2-acetylamino-3-biphenyl propanoic acid. Yield ratio: 94.3%. Spectroscopic data as Example 28.

Example 32

Preparation of (L)-2-propionyl amino-3-biphenyl propanoic acid

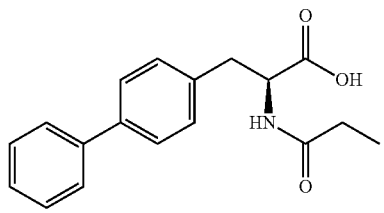 [SMILES: CCC(=O)N[C@@H](Cc1ccc(-c2ccccc2)cc1)C(=O)O]

In a dry and clean reaction bottle, add 200 ml of methanol and 10 g of (L)-2-propionyl amino-3-biphenyl propanoic acid-(R)-2-amino N,N-dimethyl-2-phenyl-acetamide salt. Elevate temperature to 90 deg C. Instill 15 g of citric acid. Maintain temperature for 5 hours. Cool down to 0 to 5 deg C. Vacuum filtrate it. Obtain 6.4 g of the product (L)-2-propionyl amino-3-biphenyl propanoic acid. Yield ratio: 91.8%. 1H NMR (500 MHz, DMSO-d6): 0.91-0.94, 2.06-2.11, 2.88-2.93, 3.08-3.12, 4.44-4.49, 7.32-7.36, 7.44-7.47, 7.57-7.59, 7.64-7.66, 8.15-8.16, 12.72; MS (m/z): 224.1 (100), 167.1 (46), 165.1 (20), 296.9 ([MH+], 1).

Example 33

Preparation of (D)-2-(N-formyl phenyl)amino-3-biphenylpropionic acid

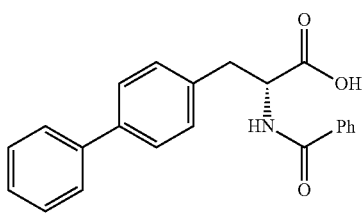 [SMILES: O=C(N[C@H](Cc1ccc(-c2ccccc2)cc1)C(=O)O)c1ccccc1]

In a dry and clean reaction bottle, add 25 ml of isopropanol and 10 g of (D)-2-(N-formyl phenyl)amino-3-biphenyl propanoic acid-(S)-amino-phenyl-methyl acetate amine salt. Elevate temperature to 10 deg C. Instill 4 g of acetic acid. Maintain temperature for 30 min. Slowly cool reaction solution down to 0 to 5 deg C. Vacuum filtrate it. Obtain 6.0 g of the product (D)-2-(N-formyl phenyl)amino-3-biphenylpropionic acid. Yield ratio: 89.7%. 1H NMR (500 MHz, DMSO-d6): 3.11-3.16, 3.23-3.26, 4.64-4.69, 7.31-7.33, 7.34-7.45, 7.46-7.48, 7.58-7.60, 7.62-7.64, 7.82-7.84, 8.77-8.78, 12.83; MS (m/z): 224.0 (100), 167.1 (30), 165.1 (16), 105.1 (7), 77.1 (15), 344.8 ([MH+], 1).

Example 34

Preparation of (L)-2-(N-para-chlorobenzoyl)amino-3-biphenyl propanoic acid

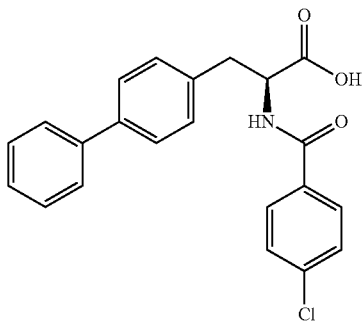

In a dry and clean reaction bottle, add 100 ml of tetrahydrofuran and 10 g of (L)-2-(N-para-chlorobenzoyl)amino-3-biphenyl propanoic acid-(R)-amino-phenyl-isopropyl acetate amine. Elevate temperature to 40 deg C. Instill 5 g of formic acid. Maintain temperature for 2.5 hours. Cool down to 10 to 20 deg C. Vacuum filtrate it. Obtain 5.3 g of the product, (L)-2-(N-para-chlorobenzoyl)amino-3-biphenyl propanoic acid. Yield ratio: 87.6%. 1H NMR (500 MHz, DMSO-d6): 3.10-3.14, 3.26-3.30, 4.61-4.66, 7.13-7.34, 7.39-7.44, 7.52-7.56, 7.61-7.63, 7.84-7.86, 8.75-8.77; MS (m/z): 224.1 (100), 167.1 (40), 165.1 (15), 139.1 (5), 111.1 (6), 378.9 ([MH+], 1).

The invention claimed is:
1. A process for preparing a compound of formula (I), or salt thereof,

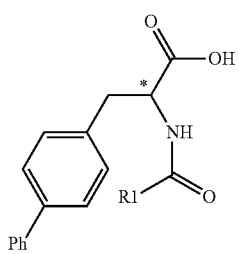

wherein
R1 is $C_{1-7}$alkyl or is substituted or unsubstituted $C_{6-10}$aryl, and
"*" means a chiral center with absolute stereochemistry (R) or (S),
comprising the steps of
i) preparing in a one-step reaction a compound of formula (III) or salt thereof,

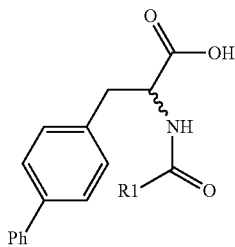

wherein
R1 is as defined for the compound of formula (I);
by reacting a compound of formula (IV), or salt thereof,

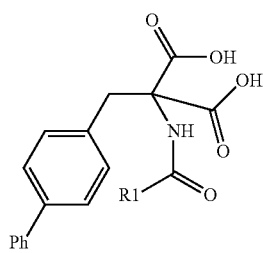

wherein
R1 is as defined for the compound of formula (I);
under decarboxylation reaction conditions to provide the compound of formula (III);

ii) treating the obtained compound of formula (III) or a salt thereof
with a chiral amine of formula (V)

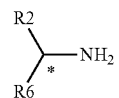

wherein
R2 is $C_{1-7}$alkyl; or is R3R4NC(=O)— or R5OC(=O)—, wherein R3 and R4 are independently selected from hydrogen or $C_{1-7}$alkyl; and R5 is $C_{1-7}$alkyl;
R6 is $C_{6-10}$aryl, and
"*" means a chiral center with absolute stereochemistry (R) or (S);
and resolving the resulting diastereomeric mixture via crystallization
to provide a composition of formula (II)

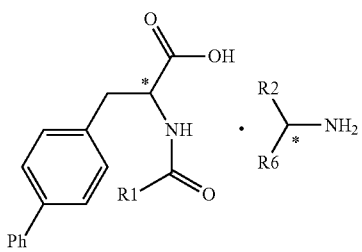

wherein
R1 is as defined for the compound of formula (I);
R2 is $C_{1-7}$alkyl; or is R3R4NC(=O)— or R5OC(=O)—, wherein R3 and R4 are independently selected from hydrogen or $C_{1-7}$alkyl; and R5 is $C_{1-7}$alkyl;
R6 is $C_{6-10}$aryl, and
"*" means a chiral center with absolute stereochemistry (R) or (S); and
iii) treating the obtained composition of formula (II),
with an acidic reagent to provide the compound of formula (I).

2. The process according to claim 1, wherein
R1 is methyl, ethyl, phenyl or para-chlorophenyl,
R2 is methyl, and
R6 is phenyl.

3. The process according to claim 2, wherein the decarboxylation reaction conditions are achieved by heating at a temperature of from 80 deg C. to 250 deg C.

4. The process according to claim 1, wherein in step (i) the decarboxylation reaction is carried out without a solvent, or in a solvent selected from water, toluene, xylene, ethylbenzene, chlorobenzene, dichlorobenzene, nitrobenzene, N,N-dimethyl formamide (DMF) and 1-methyl-2-pyrrolidone (NMP) and at the reflux temperature of said solvent.

5. The process according to claim 1, wherein
the chiral amine of formula (V) is of the formula (Va)

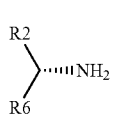

or is of the formula

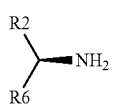

wherein R2 and R6 are as defined in claim 1,
and wherein the chiral composition of formula (II) is of the formula

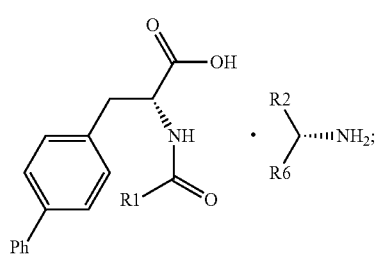

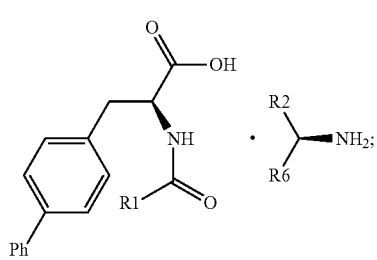

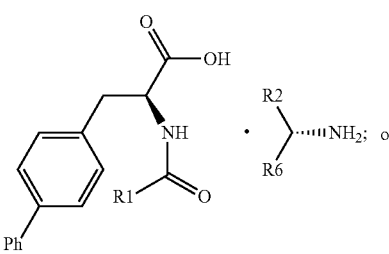

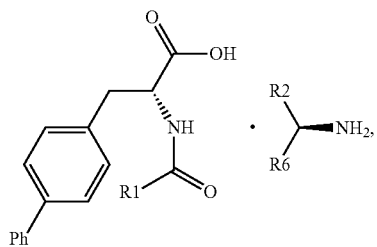

wherein R1, R2 and R6 are as defined in claim 1.

6. The process according to claim 1, wherein the chiral compound of formula (I) is of the formula (Ia),

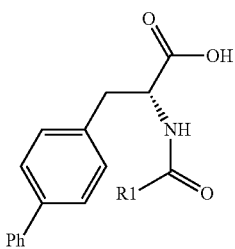

wherein R1 is as defined in claim 1; and
wherein the chiral composition of formula (II) is of the formula (IIa),

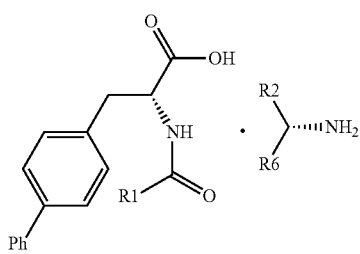

wherein R1, R2 and R6 are as defined in claim 1; and
wherein the chiral amine of formula (V) is of the formula (Va)

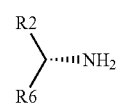

wherein R1, R2 and R6 are as defined in claim 1.

7. The process according to claim 1,
wherein the chiral compound of formula (I) is of the formula (Ib),

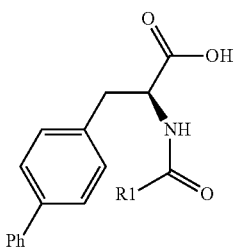

wherein R1 is as defined in claim 1; and
wherein the chiral composition of formula (II) is of the formula (IIb),

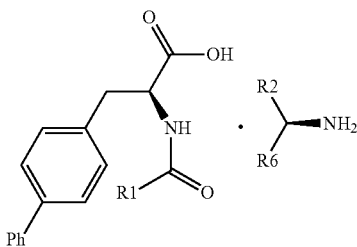

(IIb)

wherein R1, R2 and R6 are as defined in claim 1; and
wherein the chiral amine of formula (V) is of the formula (Vb)

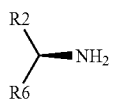

(Vb)

wherein R2 and R6 are as defined in claim 1.

8. The process according to claim 1, wherein in step (iii) the acidic reagent is an inorganic acid or an organic acid selected from hydrochloric acid, sulfuric acid, phosphoric acid, oxalic acid, citric acid, formic acid and acetic acid.

9. A process for preparing a compound of formula (I), or salt thereof,

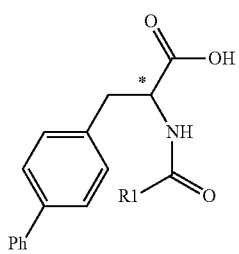

(I)

wherein
R1 is $C_{1-7}$alkyl or is substituted or unsubstituted $C_{6-10}$aryl, and
"*" means a chiral center with absolute stereochemistry (R) or (S),
comprising the steps of
i) treating a compound of formula (III) or a salt thereof

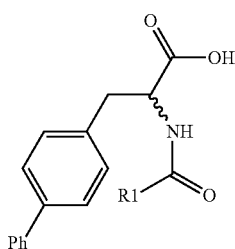

(III)

wherein
R1 is as defined for the compound of formula (I);
with a chiral amine of formula (V)

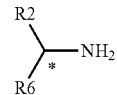

wherein
R2 is $C_{1-7}$alkyl; or is R3R4NC(=O)— or R5OC(=O)—, wherein R3 and R4 are independently selected from hydrogen or $C_{1-7}$alkyl; and R5 is $C_{1-7}$alkyl;
R6 is $C_{6-10}$aryl, and
"*" means a chiral center with absolute stereochemistry (R) or (S);
and resolving the resulting diastereomeric mixture via crystallization
to provide a composition of formula (II)

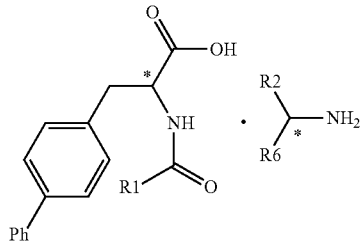

(II)

wherein
R1 is as defined for the compound of formula (I);
R2 is $C_{1-7}$alkyl; or is R3R4NC(=O)— or R5OC(=O)—, wherein R3 and R4 are independently selected from hydrogen or $C_{1-7}$alkyl; and R5 is $C_{1-7}$alkyl;
R6 is $C_{6-10}$aryl, and
"*" means a chiral center with absolute stereochemistry (R) or (S); and
ii) treating the obtained composition of formula (II), with an acidic reagent to provide the compound of formula (I).

10. The process according to claim 9, wherein
R1 is methyl, ethyl, phenyl or para-chlorophenyl,
R2 is methyl, and
R6 is phenyl.

11. The process according to claim 9, wherein the chiral amine of formula (V) is of the formula (Va)

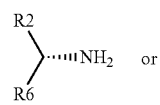

(Va)

or

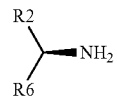

(Vb)

is of the formula
wherein R2 and R6 are as defined in claim 9,
and wherein the chiral composition of formula (II) is of the formula

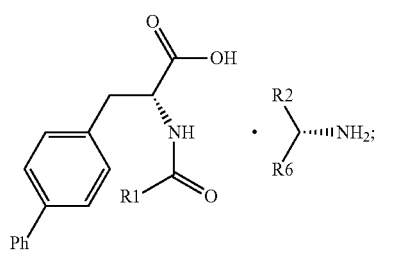
(IIa)

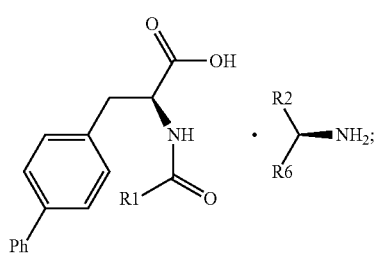
(IIb)

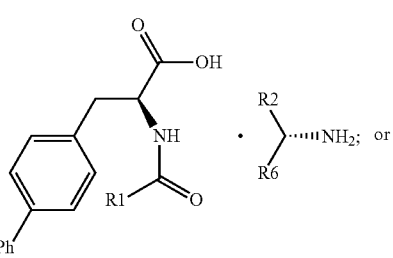
(IIc) or

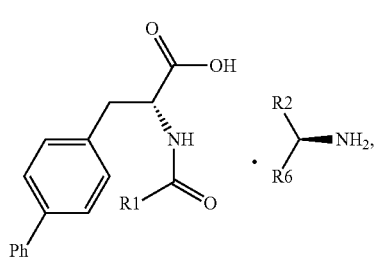
(IId), wherein R1 is methyl, ethyl, phenyl or para-chlorophenyl,
R2 is methyl, and
R6 is phenyl.

12. The process according to claim 9,
wherein the chiral compound of formula (I) is of the formula (Ia),

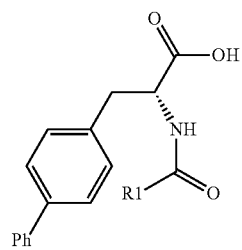
(Ia)

wherein R1 is as defined in claim 9; and
wherein the chiral composition of formula (II) is of the formula (IIa),

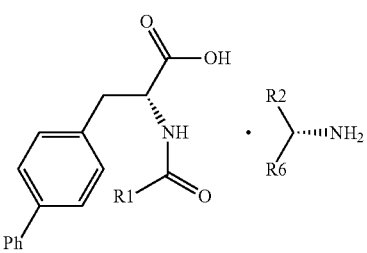
(IIa)

wherein R1, R2 and R6 are as defined in claim 9; and
the chiral amine of formula (V) is of the formula (Va)

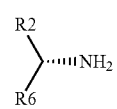
(Va)

wherein R1, R2 and R6 are as defined in claim 9.

13. The process according to claim 9,
wherein the chiral compound of formula (I) is of the formula (Ib),

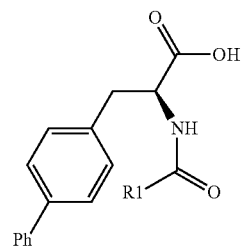
(Ib)

wherein R1 is as defined in claim 9; and
wherein the chiral composition of formula (II) is of the formula (IIb),

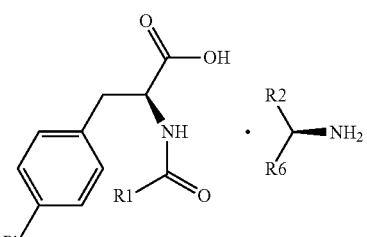
(IIb)

wherein R1, R2 and R6 are as defined in claim 9; and
the chiral amine of formula (V) is of the formula (Vb)

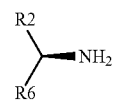
(Vb)

wherein R2 and R6 are as defined in claim 9.

14. The process according to claim 9, wherein in step (ii) the acidic reagent is an inorganic acid or an organic acid selected from hydrochloric acid, sulfuric acid, phosphoric acid, oxalic acid, citric acid, formic acid and acetic acid.

15. A method for preparing a compound of formula (I), or salt thereof,

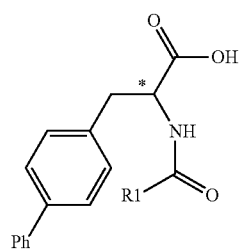
(I)

wherein
R1 is $C_{1-7}$alkyl or is substituted or unsubstituted $C_{6-10}$aryl, and
"*" means a chiral center with absolute stereochemistry (R) or (S),
comprising
treating a composition of formula (II),

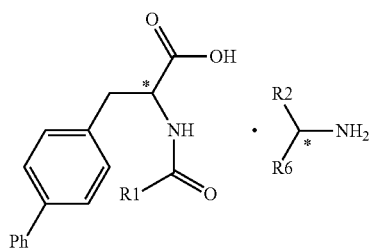
(II)

wherein
R1 is as defined for the compound of formula (I);
R2 is $C_{1-7}$alkyl; or is R3R4NC(=O)— or R5OC(=O)—, wherein R3 and R4 are independently selected from hydrogen or $C_{1-7}$alkyl; and R5 is $C_{1-7}$alkyl;
R6 is $C_{6-10}$aryl, and
"*" means a chiral center with absolute stereochemistry (R) or (S); and
with an acidic reagent
to provide the compound of formula (I).

16. The process according to claim 15, wherein
R1 is methyl, ethyl, phenyl or para-chlorophenyl,
R2 is methyl, and
R6 is phenyl.

17. The process according to claim 15, wherein the acidic reagent is an inorganic acid or an organic acid selected from hydrochloric acid, sulfuric acid, phosphoric acid, oxalic acid, citric acid, formic acid or acetic acid.

18. The process according to claim 15, wherein the chiral compound of formula (I) is of the formula (Ia),

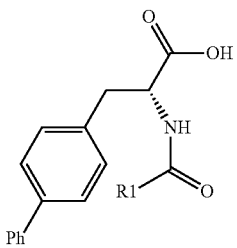
(Ia)

wherein R1 is as defined in claim 15; and
the chiral composition of formula (II) is of the formula (IIa)

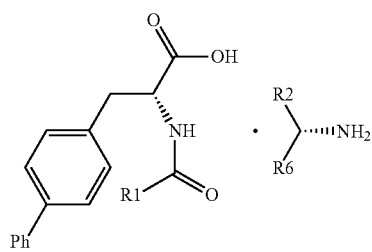
(IIa)

wherein R1, R2 and R6 are as defined in claim 15.

19. The process according to claim 15, wherein the chiral compound of formula (I) is of the formula (Ib),

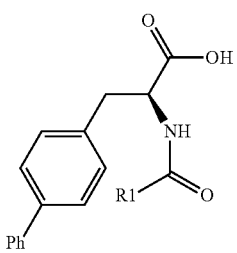
(Ib)

wherein R1 is as defined in claim 15; and
the chiral composition of formula (II) is of the formula (IIb)

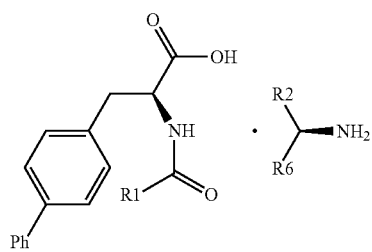
(IIb)

wherein R1, R2 and R6 are as defined in claim 15.

* * * * *